United States Patent
O'Hara

(10) Patent No.: US 7,110,819 B1
(45) Date of Patent: Sep. 19, 2006

(54) IMPLANTABLE MEDICAL DEVICE HAVING A PROTECTED CONNECTION HEADER

(75) Inventor: Casey O'Hara, Mountain View, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 199 days.

(21) Appl. No.: 10/092,666

(22) Filed: Mar. 5, 2002

(51) Int. Cl.
*A61N 1/375* (2006.01)

(52) U.S. Cl. ...................................................... 607/36

(58) Field of Classification Search ................ 607/36, 607/37, 38; 439/909
See application file for complete search history.

(56) References Cited

U.S. PATENT DOCUMENTS

| | | | |
|---|---|---|---|
| 3,757,789 A * | 9/1973 | Shanker ....................... 607/37 |
| 5,895,414 A * | 4/1999 | Sanchez-Zambrano ....... 607/36 |
| 6,327,502 B1 * | 12/2001 | Johansson et al. ............ 607/36 |
| 6,498,951 B1 * | 12/2002 | Larson et al. ................. 607/36 |
| 6,505,073 B1 * | 1/2003 | Gramse ........................ 607/37 |
| 2003/0144707 A1 * | 7/2003 | Ruben et al. ................. 607/37 |

* cited by examiner

*Primary Examiner*—Kennedy Schaetzle
(74) *Attorney, Agent, or Firm*—Steven M. Mitchell

(57) ABSTRACT

An implantable medical device having a sealed housing forming a chamber containing rhythm management circuitry. The housing has an exterior defining a recess in which a header is received. The header has a number of lead bores, and includes an electrical contact within each bore, with each contact connected to the circuitry in the housing. The housing recess encompassing a major portion of the header, which may be positioned away from the corners of the housing, and which may be formed to avoid protruding from the housing. The recess may enclose at least three orthogonal sides of the header, and may include opposed parallel side capturing the header.

9 Claims, 6 Drawing Sheets

IMPLANTABLE MEDICAL DEVICE HAVING A PROTECTED CONNECTION HEADER

FIELD OF THE INVENTION

This invention relates to implantable medical devices, and more particularly to structural configurations of implantable cardioverter/defibrillators.

BACKGROUND OF THE INVENTION

Implantable Cardioverter Defibrillators (ICDs) are implanted in patients susceptible to cardiac tachyarrhythmias including atrial and ventricular tachycardias and atrial and ventricular fibrillation. Such devices typically provide cardioversion or defibrillation by delivering low voltage pacing pulses or high voltage shocks to the patient's heart, typically about 500–800V. The ICD operates by detecting a fast heart rate or tachyarrhythmia, upon which a battery within the device housing is coupled via an inverter to a high voltage capacitor or capacitor pair to charge the capacitors. When the capacitor reaches a desired voltage, charging is stopped and the capacitors are discharged under control of a microprocessor to provide a therapeutic shock to the patient's heart.

ICDs are contained in compact housings. Housings are typically flat bodies having parallel major surfaces, and a periphery shaped to closely contain internal components to minimize device volume. The periphery is normally formed of straight or convexly rounded segments, with any corners and edged smoothly radiused for patient comfort.

To provide communication between the device circuitry and leads that extend to a patient's heart, the housing includes a connector header. The header is a body that defines bores to receive the ends of the leads, and has electrical contacts in the bores that extend through the wall of the housing via insulated sealed feedthroughs to internal circuitry. Headers are typically formed of inert material such as epoxy, which adheres to the housing surface. Housings normally define an inlet space for the header, so that the overall housing and header shape has the desired smooth form.

In existing devices, the header is formed on one corner of the housing, so that the housing is notched at the corner, and the header fills in the notch. While effective, such an arrangement may have certain disadvantages in certain applications or circumstances. With the protruding header forming the corner of the device, it is exposed to possible damage. If the device were dropped or struck against a hard surface on the protruding header, there is a risk that the header may be damaged or dislodged. In addition, with the header typically contacting the housing at only two surfaces defining the notch, and with these two surfaces being obtusely angled with respect to each other, the housing provides only limited structural support for the header. Even in instances in which the device is not dropped, the forces generated by lead insertion, and at all other stages of manufacturing, shipping, handling, and installation, may generate unwanted stresses.

Moreover, with the electrical feed-through located at one corner of the housing, connections to internal components away from the header corner require longer conductors, increasing device volume. Also, existing devices are limited to only a single housing surface to be penetrated by feed-throughs, limiting design flexibility for internal components.

In addition, the process of molding a corner-located header is challenging. Normally, a silicone mold defining the outer surface of the header is attached to a housing, and the defined chamber is filled with epoxy. However, with the protruding header exterior defined only by the flexible silicone mold, there may be unwanted variations in the final shape, with a flush resulting surface transition between the housing and header being potentially compromised.

SUMMARY OF THE INVENTION

The disclosed embodiment overcomes the limitations of the prior art by providing an implantable medical device and in particular an implantable cardiac rhythm management device having a sealed housing forming a chamber containing rhythm management circuitry. The housing has an exterior defining a recess in which a header is received. The header has a number of lead bores, and includes an electrical contact within each bore, with each contact connected to the circuitry in the housing. The housing recess encompasses a major portion of the header, which may be positioned away from the corners of the housing, and which may be formed to avoid protruding from the housing. The recess may enclose at least three orthogonal sides of the header, and may include opposed parallel sides capturing the header.

BRIEF DESCRIPTION OF THE DRAWINGS

Further features and advantages of the present invention may be more readily understood by reference to the following description taken in conjunction with the accompanying drawings, in which.

DETAILED DESCRIPTION OF A PREFERRED EMBODIMENT

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
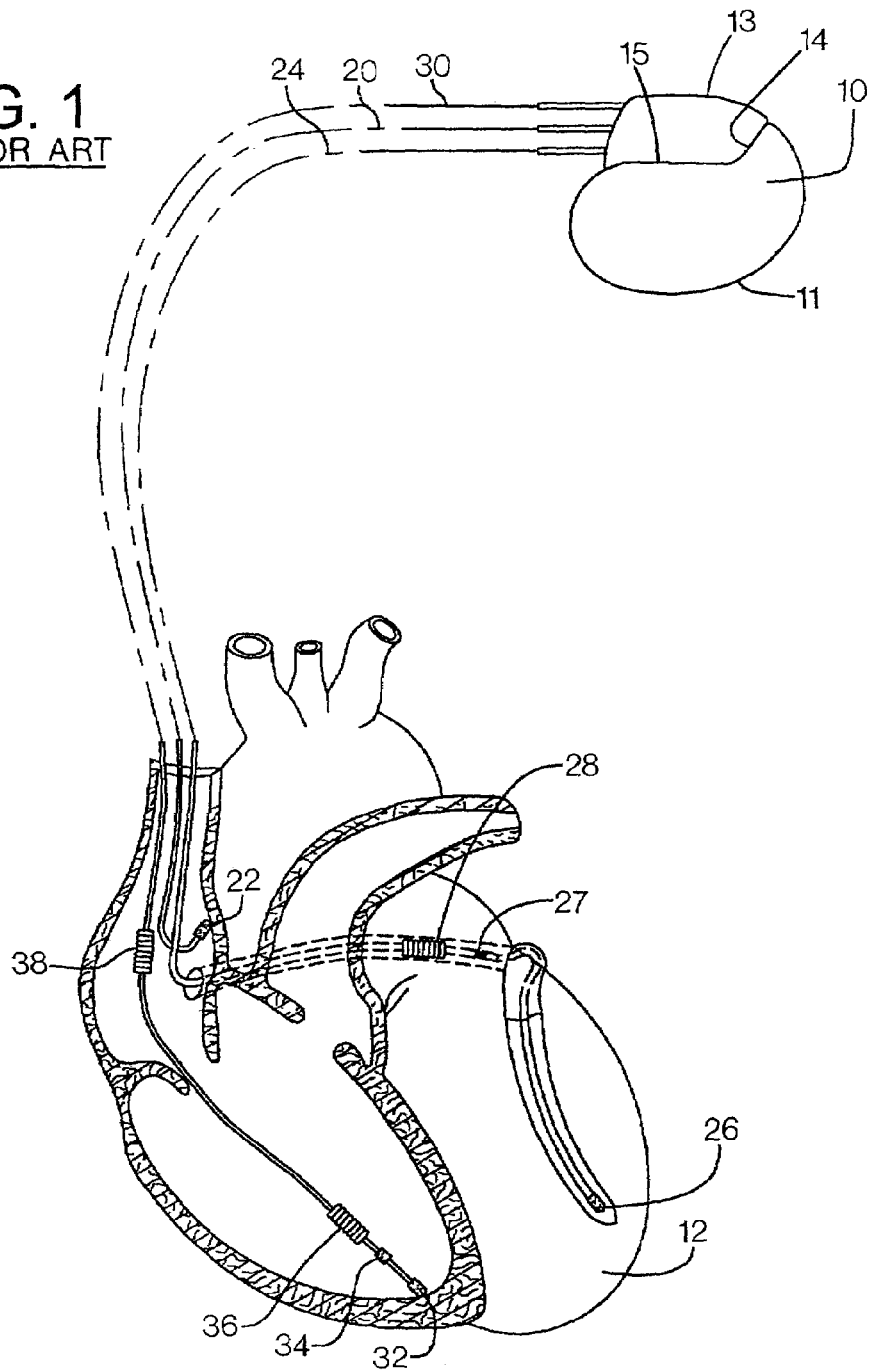
FIG. 1 is a simplified diagram illustrating an implantable stimulation device, having a prior art housing and header form, in electrical communication with at least three leads implanted into a patient's heart for delivering multi-chamber stimulation and shock therapy.

As shown in FIG. 1, there is a stimulation device 10 in electrical communication with a patient's heart 12 by way of three leads, 20, 24 and 30, suitable for delivering multi-chamber stimulation and shock therapy. The device 10 is shown in a form found in the prior art, while the rest of the elements and description are consistent with the preferred embodiment of the invention. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

The prior art form of the device 10 has a hollow, sealed metal housing 11 containing the circuitry discussed below, and a header 12 to which the leads are connected. The overall prior art device shape is a flat body with a rounded periphery. The header essentially forms one corner of the device, and protrudes from the housing. The header is attached to the housing at a pair of obtusely angled housing surfaces 14, 15, which form a shallow recess, and each of which faces away from the rest of the housing. The angle of the surfaces 14, 15 is about 120°.

To sense left atrial and ventricular cardiac signals and to provide left chamber pacing therapy, the stimulation device 10 is coupled to a "coronary sinus" lead 24 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and a Superior Vena Cava (SVC) coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
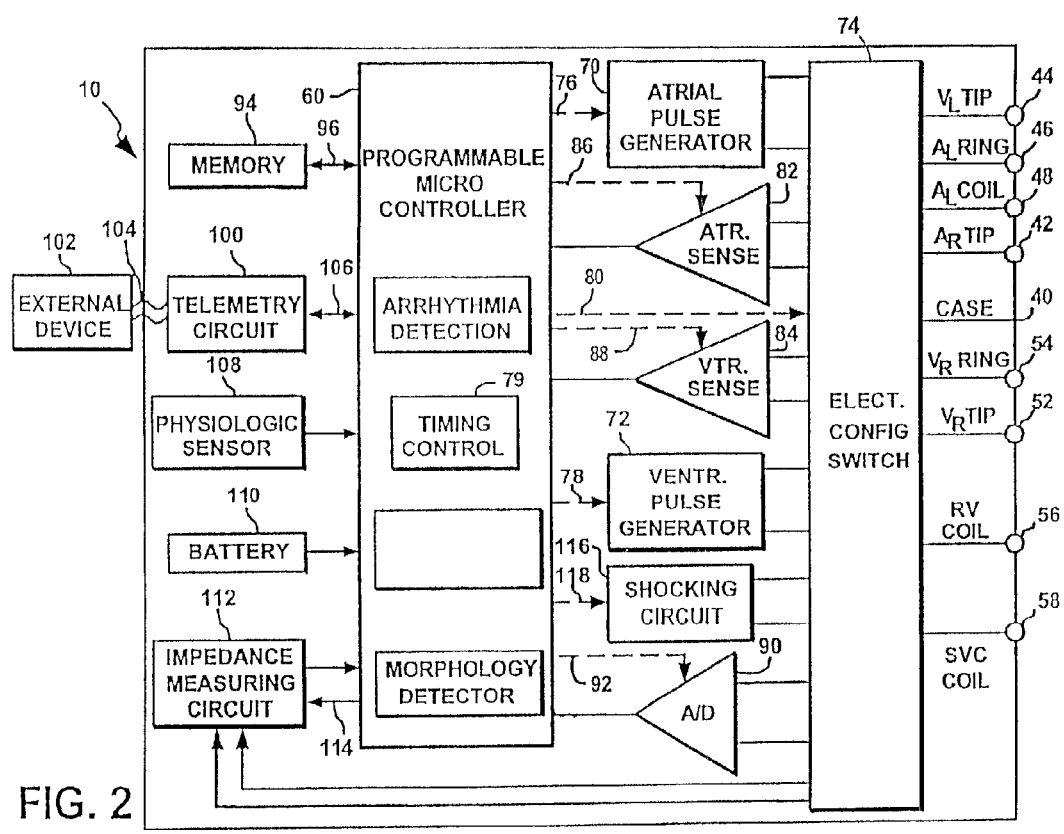
FIG. 2 is a functional block diagram of a multi-chamber implantable stimulation device according to the preferred embodiment illustrating the basic elements of a stimulation device which can provide cardioversion, defibrillation and pacing stimulation in four chambers of the heart.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can," "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal (AR TIP) 42 adapted for connection to the atrial tip electrode 22.

To achieve left chamber sensing, pacing and shocking, the connector includes at least a left ventricular tip terminal (VL TIP) 44, a left atrial ring terminal (AL RING) 46, and a left atrial shocking terminal (AL COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal (VR TIP) 52, a right ventricular ring terminal (VR RING) 54, a right ventricular shocking terminal (RV COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A—A) delay, or ventricular interconduction (V—V) delay, etc.) as well as to keep track of the timing of refractory periods, PVARP intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104. In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V—V Delay, etc.) at which the atrial and ventricular pulse generators, 70 and 72, generate stimulation pulses.

The stimulation device additionally includes a battery 110 which provides operating power to all of the circuits shown in FIG. 2. For the stimulation device 10, which employs shocking therapy, the battery 110 must be capable of operating at low current drains for long periods of time (preferably less than 10 μA), and then be capable of providing high-current pulses (for capacitor charging) when the patient requires a shock pulse (preferably, in excess of 2 A, at voltages above 2 V, for periods of 10 seconds or more). The battery 110 must also have a predictable discharge characteristic so that elective replacement time can be detected. Accordingly, the device 10 preferably employs lithium/silver vanadium oxide batteries, as is true for most (if not all) current devices.

The stimulation device 10 further includes a magnet detection circuitry (not shown), coupled to the microcontroller 60. It is the purpose of the magnet detection circuitry to detect when a magnet is placed over the stimulation device 10, which magnet may be used by a clinician to perform various test functions of the stimulation device 10 and/or to signal the microcontroller 60 that the external programmer 102 is in place to receive or transmit data to the microcontroller 60 through the telemetry circuits 100.

As further shown in FIG. 2, the device 10 is shown as having an impedance measuring circuit 112 which is enabled by the microcontroller 60 via a control signal 114.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high energy (11 to 40 Joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 3:
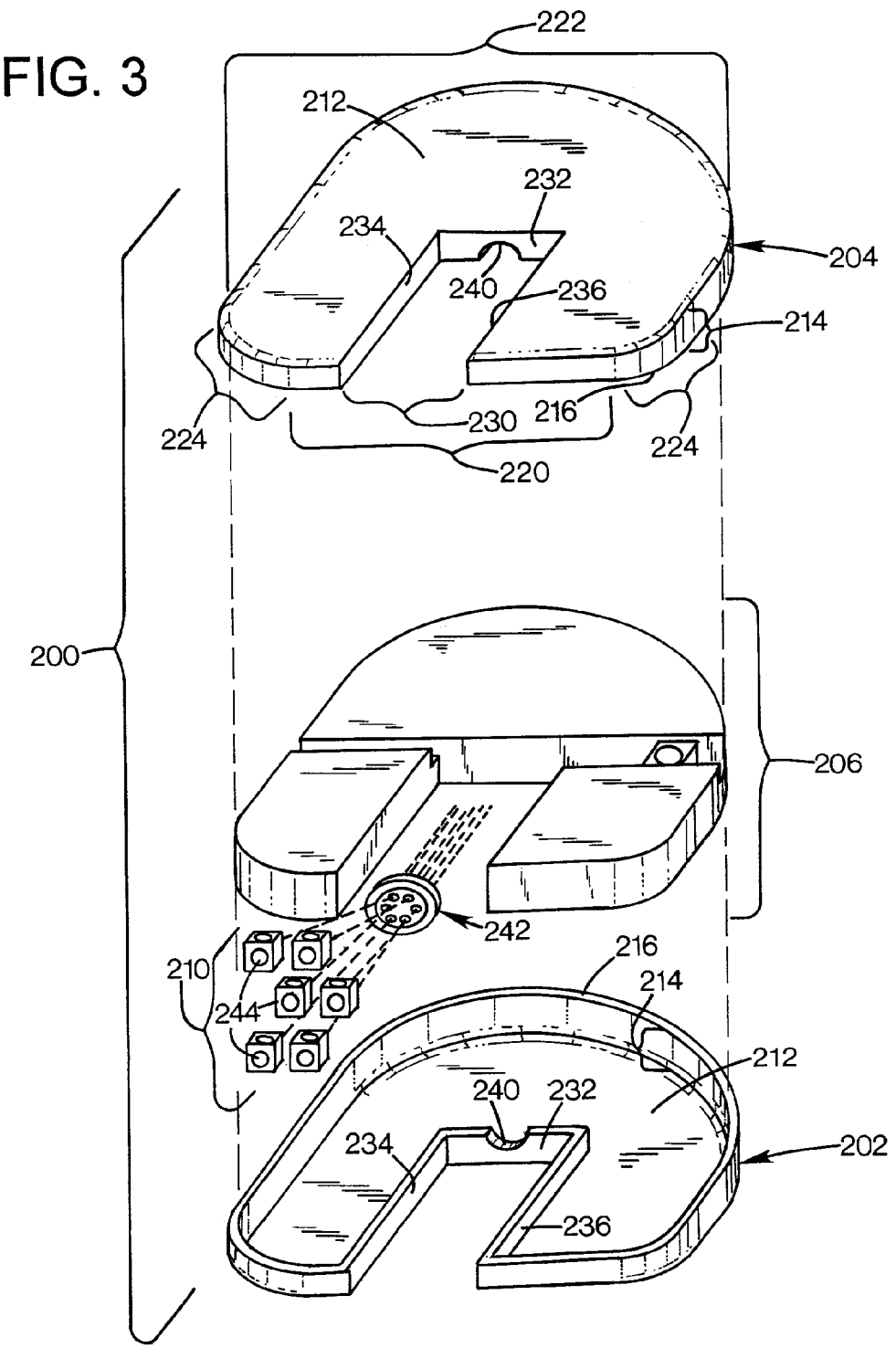
FIG. 3 is an exploded view of a preferred embodiment of the invention.

FIG. 3 illustrates an ICD 200 according to a preferred embodiment of the invention. The ICD includes a lower housing portion 202, an upper housing portion 204, and internal circuitry and electrical components 206 (as noted in detail above with respect to FIG. 2.) A set of header components 210 is also included.

The housing portions are mirror images of each other in the illustrated embodiment, although this is not the case in alternative embodiments discussed below. Each portion has a flat major panel 212 with a sidewall 214 extending about the periphery and having a rim edge 216 facing away from the panel 212 and occupying a plane parallel to and offset from the panel. The peripheries of the housing portions are the same, so that the rims align without a gap when joined, so that they may be welded to seal the components 206 in a chamber defined by the housing.

The shape of the periphery of the housing portions, and therefore the finished housing, provides certain advantages. The periphery is shaped to provide a comfortably rounded exterior, so that there are no sharp corners or protrusions that might generate sharp pressure against a patient's tissue. The shape is also designed to closely enclose the components, minimizing overall volume. The overall planar shape provides a relatively thin housing that does not noticeably protrude in a subcutaneous implantation, and which also provides patient comfort. The peripheral shape is made up of segments that are curved convex arcs of one or more radii, and straight portions in some embodiments, such as shown.

In the illustrated embodiment, the periphery has essentially a "D" shape. It includes a straight side 220, and a gently curved round side 222. The round side is not necessarily a precise semi-circle, but varies in radius. The sides 220 and 222 are joined at more sharply radiused corner arcs 224, which are the smallest radius portions of the periphery. The straight side is considered to have an infinite radius of curvature. All peripheral segments are convex or straight; a convex segment would lead to limited device volume relative to the device's overall longest dimension.

A substantially rectangular or parallelogramic housing inlet 230 is defined centrally on the straight side 220 of the housing. The inlet includes a rear wall 232 parallel to the straight side (or roughly parallel to the center of the side for an embodiment in which a large radius arc replaces the straight side as illustrated below.) The inlet has side walls 234, 236 that are parallel to and face each other, and which extend from the rear wall to the peripheral edge 220. The rear and side walls are perpendicular to the outer surface of the panel 212, and meet the panel at more sharply defined corner edges. The rear wall 232 of each housing portion defines a central semi-circular cutout 240 that forms half of a circular aperture when the housing portions are joined. The inlet is positioned away from the high radius device corners, and is on a device periphery segment having the least (zero, in this example) curvature of any periphery segments.

Figure 4:
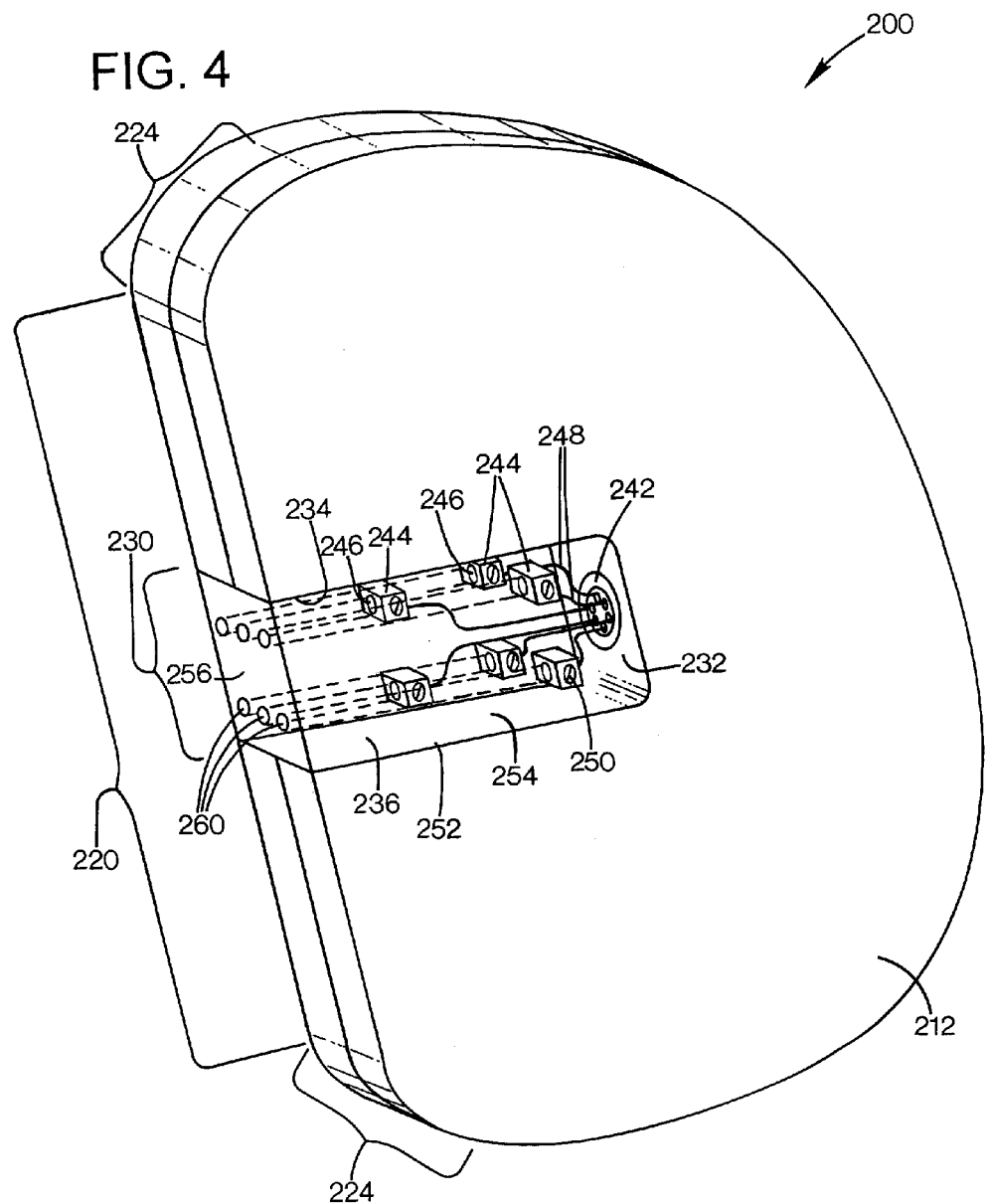
FIG. 4 is a perspective view of the embodiment of FIG. 3.

As also shown in FIG. 4, the header component set 210 includes a circular feedthrough element 242 that is sized to be closely received in the aperture 240, and hermetically sealed thereto. The feedthrough element has an electrically insulating body, and a number of conductive wires that pass through the body to provide connections to internal components. A set of header contacts 244 are each connected to a respective wire, and are electrically isolated from each other. Each contact is a cube defining a bore 246 for receiving an end of a lead wire 248, and having a lateral set screw 250 for securing the lead wire end in the bore.

A header body 252 fills the recess 230 in the housing. The header has an exterior surface flush with the exterior housing surfaces, with opposed side faces 254 coplanar with the exterior surfaces of panels 212, and an edge face 256 coplanar and flush with the straight side surface 220 of the housing. The header body encapsulates the contacts 244, and defines a bore 260 extending perpendicularly from the edge face 256 to each of the contacts, with the bores being coaxial with the contact bores, and the contact bore surfaces exposed. This permits lead ends to be inserted in the bores for contacting the contacts. The contacts are positioned with the set screws accessible from the side faces, either by placement of contacts at the surface, or by a bore to access internally placed contacts. The header body is cast in place from epoxy or another inert resin compound, and is adhered to the housing inlet wall surfaces 232, 234, 236.

In a cross section taken perpendicular to the line defined by the straight edge 220 of the housing, the exposed header surfaces 254, 256 have a constant cross section, regardless of the location along the line. This cross section is the same as the cross section of the housing itself just beyond the header. Accordingly, the housing and header have an essentially rectangular cross section in this area. The fact that no portion of the header surface protrudes above the surrounding housing provides an improved resistance to impact. The device may be placed against or struck against a flat surface, and the more robust metal housing will make the first and/or primary contact, and bear most or all of such stresses.

Moreover, even if the header surface were struck by an object with a convex surface, the header resists damage or dislocation by its configuration. In the illustrated embodiment, the header is adhered to the housing on three of six sides, and is thus supported in two orthogonal directions. In addition, the use of parallel inlet surfaces 234, 236 mechanically captures the header, further supporting the header against damage or dislodgment by a focused blow. And the limitation of the number of exposed surfaces limits the probability of such a blow contacting the header. Any blow striking the edge face of the header will tend to generate compression against the rear surface 232, which readily provides support, and avoid shearing Forces that might delaminate the header from the housing. In the illustrated embodiment, the peripheral surfaces of the header are more than 75% captured by contact with the housing, in contrast to the prior art device, with is slightly less than 50% captured, and which protrudes.

The device is assembled by positioning the components and feed through in the housing, and welding the housing at the seam for a hermetic seal. The contacts are then connected to the wires of the feed through. To form the header, removable core pins are inserted into the contact bores to maintain them open, and an elastomeric mold is placed about the housing recess. The mold has internal surfaces that are essentially flat across each housing face, and flat along the edge face, having the same cross sectional profile as the finished device. Such a mold is more readily used, and less subject to distortion than a mold that defines many sides of a protruding header, as the preferred mold is supported more securely by the surrounding housing surfaces. Epoxy is injected into the cavity defined by the mold, and after the epoxy hardens, the mold and core pins are removed to provide the finished header.

Figure 5:
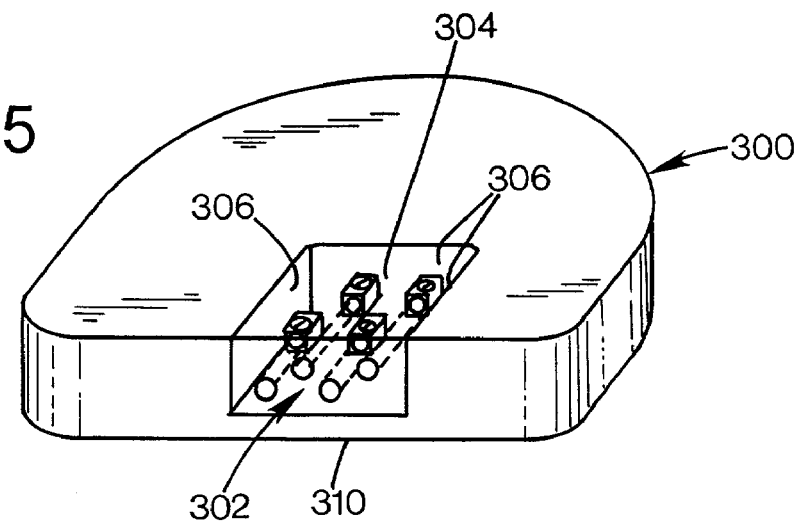
FIG. 5 is a perspective view of an alternative embodiment of the invention.

FIG. 5 shows an alternative embodiment device 300 in which the header 302 is received in an inlet 304 in the housing, with similar peripheral support from sidewalls 306 of the inlet. However, unlike the embodiment of FIG. 4, in which the header extends fully through the thickness of the device to both major panel surfaces, the header is also supported by a surface panel portion 310 extending entirely beneath the header, in line with the major surface panel of the lower housing portion. This header is thus supported on a third orthogonal side. In variations on this, a corner header may be supported in three orthogonal directions by three inlet surfaces each perpendicular to the other two, if the protruding corner can be accepted. The illustrated embodiment requires that all the contact set screws be accessed from the one side opposite from the panel 310.

Figure 6:
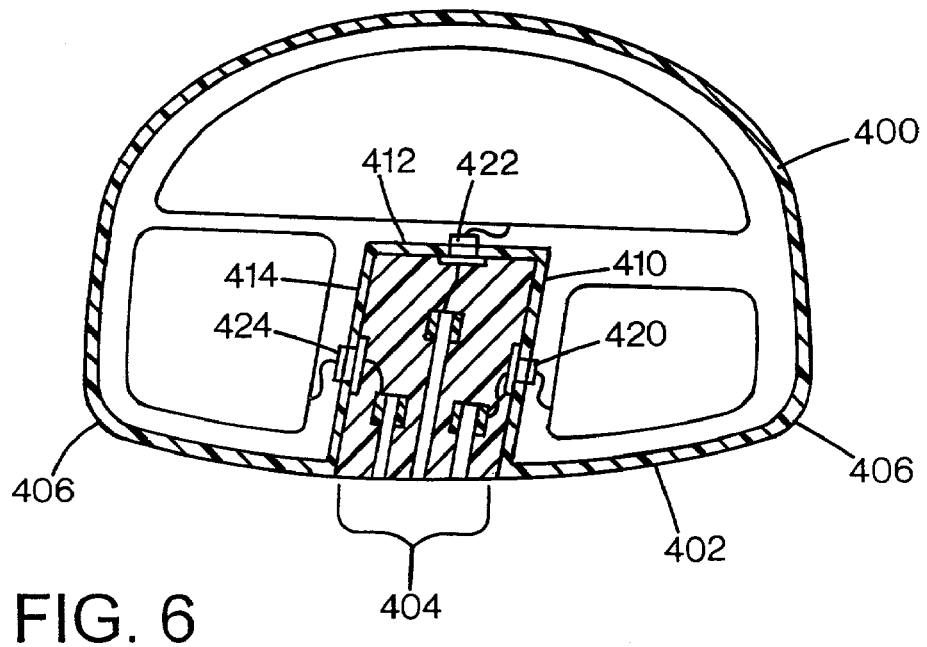
FIG. 6 is a cross sectional plan view of another alternative embodiment of the invention.

FIG. 6 shows an alternative embodiment device 400 in which the periphery includes a gently curved edge 402 having the largest radius of any of the peripheral segments. The header 404 is centered on this side, away from small-radius corners 406. For all possible orientations in which the device may strike a flat surface, this position of the header minimizes the probability that the header makes first contact with the surface.

The FIG. 6 embodiment also includes another optional feature. With inlet sidewalls 410, 412, 414 facing in different directions, and toward different components, a header 420, 422, 424 may be positioned in each side wall, and provide convenient short-path wiring communication to a respective component or circuit portion.

Figure 7:
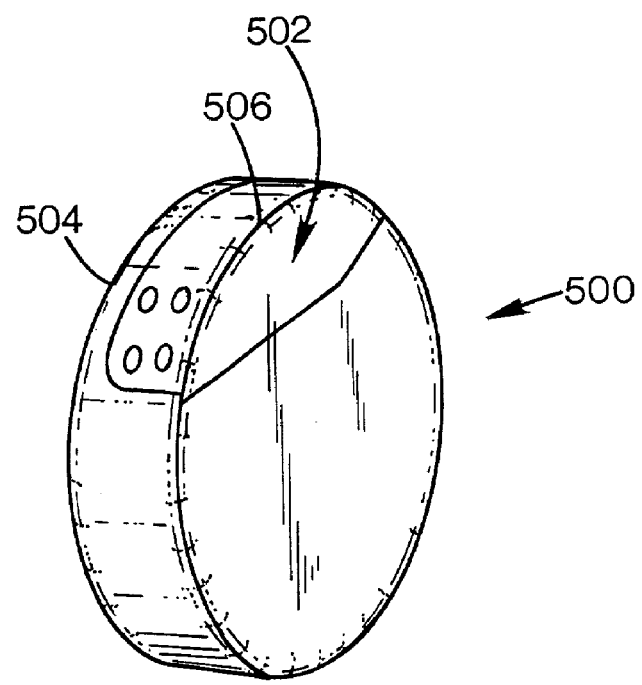
FIG. 7 is a perspective view of another alternative embodiment of the invention.

While described in terms of a preferred embodiment, the invention need not be so limited. For instance FIG. 7 shows an alternative embodiment device 500 in which a header 502 is located at once end of the housing, which may be a corner or curve of small radius. However, the header is supported by a housing flange 504 that extends from one of the major planar surfaces of the housing to prevent any portion of the header from extending beyond the housing. While the header is supported on only two orthogonal sides, one of those sides is in the plane of the device housing and both attached surfaces are relatively large compared to the overall exposed surface area of the header. Moreover, the point 506 that is furthest from any housing portion is spaced apart from any such portion by a relatively small distance.

Figure 8:
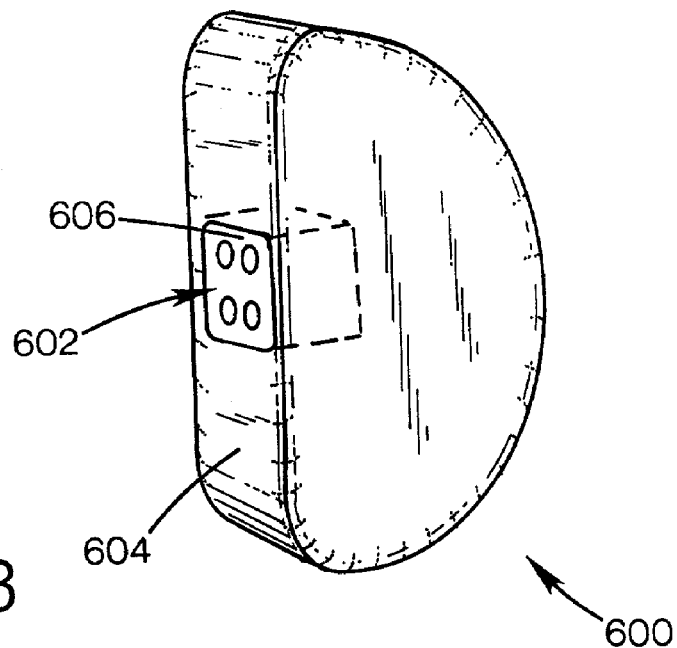
FIG. 8 is a perspective view of another alternative embodiment of the invention.

FIG. 8 shows an alternative embodiment device 600 in which a header 602 is inset into a single edge surface 604 of the device. This results in the header being supported on 5 of 6 sides, and having no protruding portion. The header has only one exposed planar surface 606 that is flush with the surrounding housing surface.

What is claimed is:

1. An implantable medical device, comprising:
   a sealed housing defining a chamber containing circuitry;
   the housing having an exterior defining a recess;
   a header received in the recess;
   the header having a body defining a plurality of lead bores, and including an electrical contact within each bore, each contact connected to the circuitry in the housing; and
   the housing recess encompassing a major portion of the header, wherein the recess has a plurality of recess surfaces abutting the header, each recess surface having at least a portion angularly offset from another of the surfaces, and wherein at least a plurality of the surfaces include a conductive feed-through extending from the housing chamber to the header.

2. An implantable cardiac rhythm management device, comprising:
   a sealed housing defining a chamber containing rhythm management circuitry;
   the housing being a flat body with opposed major faces, and having a periphery defining a recess;
   a header received in the recess;
   the header having a body defining a plurality of lead bores, and including an electrical contact within each bore, each contact connected to the circuitry in the housing; and
   the housing recess having recess surfaces abutting the header in at least three orthogonal directions.

3. The device of claim 2 wherein the recess includes at least a pair of opposed surfaces between which the header is received.

4. The device of claim 3 wherein the opposed surfaces are parallel to each other.

5. The device of claim 2 wherein the peripheral edge includes a straight edge portion, and wherein the recess is defined at an intermediate portion of the straight edge portion.

6. An implantable medical device, comprising:
   a sealed housing defining a chamber containing rhythm management circuitry;
   the housing being a flat body with opposed major faces, and having a periphery defining a recess;
   a header received in the recess;
   the recess having recess surfaces abutting the header in at least three orthogonal directions;
   the header having a body defining a plurality of lead bores, and including an electrical contact within each bore, each contact connected to the circuitry in the housing; and
   the periphery edge including several edge segment portions having different degrees of curvature, and wherein the recess is defined on an edge segment having the lowest degree of curvature.

7. The device of claim 6 wherein the housing periphery includes a corner portion having a selected radius of curvature less than that of at least another portion of the peripheral edge, and wherein the recess is positioned away from the corner portion.

8. The device of claim 6 wherein the medical device comprises a cardiac rhythm management device.

9. An implantable medical device, comprising:
   a sealed housing defining a chamber containing circuitry;
   the housing having an exterior defining a recess;
   a header received in the recess;
   the header having a body defining a plurality of lead bores, and including an electrical contact within each bore, each contact connected to the circuitry in the housing; and
   the housing recess encompassing a major portion of the header, the recess including at least a pair of parallel opposed surfaces between which the header is received.

* * * * *